US012806403B2

(12) United States Patent
Ferret et al.

(10) Patent No.: US 12,806,403 B2
(45) Date of Patent: Nov. 24, 2026

(54) PUMP MONITORED BY SENSOR

(71) Applicant: NEXTKIDNEY SA, Lausanne (CH)

(72) Inventors: Ludovic Ferret, Lausanne (CH); Matthieu Tardivon, Lausanne (CH); Séverin Leven, Lausanne (CH)

(73) Assignee: NEXTKIDNEY SA, Lausanne (CH)

( * ) Notice: Subject to any disclaimer, the term of this patent is extended or adjusted under 35 U.S.C. 154(b) by 0 days.

(21) Appl. No.: 19/112,777

(22) PCT Filed: Sep. 28, 2023

(86) PCT No.: PCT/IB2023/059690
§ 371 (c)(1),
(2) Date: Mar. 18, 2025

(87) PCT Pub. No.: WO2024/069521
PCT Pub. Date: Apr. 4, 2024

(65) Prior Publication Data
US 2026/0097157 A1 Apr. 9, 2026

(30) Foreign Application Priority Data
Sep. 29, 2022 (EP) .................................... 22198816

(51) Int. Cl.
*A61M 60/279* (2021.01)
*A61M 1/14* (2006.01)
(Continued)

(52) U.S. Cl.
CPC .......... *A61M 60/279* (2021.01); *A61M 1/155* (2022.05); *A61M 1/34* (2013.01);
(Continued)

(58) Field of Classification Search
CPC .. F04B 43/1253; F04B 43/1284; F04B 43/12; F04B 53/22; F04B 43/1292;
(Continued)

(56) References Cited

U.S. PATENT DOCUMENTS 5,215,450 A * 6/1993 Tamari ................ F04B 43/0072 138/119
8,052,399 B2 * 11/2011 Stemple .............. F04B 43/1284 417/476
(Continued)

FOREIGN PATENT DOCUMENTS

EP 4098290 A1 12/2022
WO 2011101430 A1 8/2011

OTHER PUBLICATIONS

International Search Report for PCT/IB2023/059690, mailed Jan. 16, 2024, 5 pages.
(Continued)

*Primary Examiner* — Peter J Bertheaud
(74) *Attorney, Agent, or Firm* — Nixon & Vanderhye P.C.

(57) ABSTRACT

The present document discloses a medical pumping system (20) for moving a fluid through a tube, which may comprise a machine having a motor (24) and a drive mechanism (25), and a pump head configured to be removably coupled to the drive mechanism of the machine. The machine may comprise an inductive sensor (26) and at least one processor (28) connected to the motor and the inductive sensor. The pump head may comprise a metallic element (32) intended to cooperate with the inductive sensor of the machine.

15 Claims, 3 Drawing Sheets

(51) Int. Cl.

| | |
|---|---|
| ***A61M 1/34*** | (2006.01) |
| ***A61M 5/142*** | (2006.01) |
| ***A61M 5/168*** | (2006.01) |
| ***A61M 60/113*** | (2021.01) |
| ***A61M 60/37*** | (2021.01) |
| ***A61M 60/441*** | (2021.01) |
| ***A61M 60/538*** | (2021.01) |
| ***F04B 43/12*** | (2006.01) |
| ***F04B 49/06*** | (2006.01) |
| ***F04B 51/00*** | (2006.01) |
| ***F04B 53/22*** | (2006.01) |

(52) U.S. Cl.

CPC .... *A61M 5/14232* (2013.01); *A61M 5/16831* (2013.01); *A61M 60/113* (2021.01); *A61M 60/37* (2021.01); *F04B 43/12* (2013.01); *F04B 43/1253* (2013.01); *F04B 43/1284* (2013.01); *F04B 43/1292* (2013.01); *F04B 49/065* (2013.01); *F04B 51/00* (2013.01); *F04B 53/22* (2013.01); *A61M 1/154* (2022.05); *A61M 60/441* (2021.01); *A61M 60/538* (2021.01); *A61M 2205/12* (2013.01); *A61M 2205/3317* (2013.01); *A61M 2205/3365* (2013.01); *A61M 2205/50* (2013.01)

(58) Field of Classification Search

CPC ... F04B 49/065; F04B 51/00; A61M 5/14232; A61M 60/279; A61M 2205/50; A61M 2205/12; A61M 2205/3317; A61M 1/34; A61M 60/37; A61M 2205/3365; A61M 5/16831; A61M 1/155; A61M 60/113

See application file for complete search history.

(56) References Cited

U.S. PATENT DOCUMENTS

| | | | | |
|---|---|---|---|---|
| 10,124,108 | B2 * | 11/2018 | Stefani | A61M 1/3656 |
| 10,381,963 | B2 * | 8/2019 | Kitano | A61M 60/538 |
| 10,947,966 | B2 * | 3/2021 | Stacey | F04B 49/10 |
| 11,092,148 | B2 * | 8/2021 | Thiebaud | F04B 43/0009 |
| 2001/0021817 | A1 | 9/2001 | Brugger et al. | |
| 2005/0209563 | A1 * | 9/2005 | Hopping | A61M 1/1607<br>604/151 |
| 2010/0209263 | A1 | 8/2010 | Mazur | |
| 2015/0037168 | A1 * | 2/2015 | Faccioli | F04B 49/065<br>417/18 |
| 2019/0024655 | A1 | 1/2019 | Donaldson | |

OTHER PUBLICATIONS

Written Opinion of the ISA for PCT/IB2023/059690, mailed Jan. 16, 2024, 5 pages.

Search Report for EP22198816.5 dated Feb. 24, 2023, 6 pages.

* cited by examiner

PUMP MONITORED BY SENSOR

This application is the U.S. national phase of International Application No. PCT/IB2023/059690 filed Sep. 28, 2023, which designated the U.S. and claims priority to EP Patent Application No. 22198816.5 filed Sep. 29, 2022, the entire contents of each of which are hereby incorporated by reference.

TECHNICAL FIELD

The present disclosure relates to a medical system comprising a pump device intended to move a fluid in a controlled manner, for example in the dialysis treatment field.

BACKGROUND

In many treatments, pump flow is a critical parameter, and any uncontrolled change in this parameter can result in significant risk to the patient.

Accurate measurement of a medical pump's rotational speed may be essential for certain types of treatment, for example to guarantee the medical effect, but also for patient safety. For example, in hemodialysis treatment, the pump flow rate is very important because it can induce more or less ultrafiltration (UF) during treatment and impact toxin clearance as well. Therefore, the speed of the pump head is a very important data which must be controlled precisely. In case where the pump is a peristaltic pump, the rotation of the rollers support should be controlled.

Moreover, when the peristaltic pump is used with a drive mechanism driving the pump head by friction, slippage can occur. Therefore, the driving needs to be monitored.

But the accuracy of this monitoring may depend on the sensor used. Different solutions have been tested and the main drawbacks of the tested solutions are (for example):

- Optical sensor and a white label printed on the rollers support. This solution comprised several drawbacks, in particular the optical sensor became dirty over time, and it is sensitive to possible reflections and other optical emitters (e.g., ambient light, other sensor . . . ). The optical sensor only allows the detection of one full revolution (low resolution), does not provide the rotation direction information, and eventually needed a factory calibration.
- Galvanic sensor: risk of oxidation on the contact over time due to the dialysate solution and mechanical wear,
- Magnetic sensor too expensive due to the magnet in the disposable cartridge,
- Capacitive sensor too sensitive to the relative position of the cartridge and to EMI.

SUMMARY

This general description is provided to introduce a selection of concepts in a simplified form that are further described below in the Detailed Description. This general description is not intended to necessarily identify key features or essential features of the claimed subject matter, nor is it intended as an aid in determining the scope of the claimed subject matter.

A first aspect of the disclosure provides a medical pumping system for moving a fluid through a tube, the system may include or comprise:

- A machine which may comprise at least one of a motor and a drive mechanism, and
- A pump head which may be configured to be removably coupled to the drive mechanism of the machine.

The machine may comprise an inductive sensor and at least one processor (or processing device) connected to the motor and the inductive sensor. The pump head may comprise a metallic element (for example only one element comprising metal) intended to cooperate with the inductive sensor of the machine. The at least one processor may be configured to determine (or process or monitor or detect) a defective drive or a speed of the pump head based on the data received from the inductive sensor.

The motor may be configured or adapted to drive a rotary motion of the pump head via the drive mechanism when the drive mechanism and the pump head is operatively coupled.

The at least one processor may be configured to monitor a data relating to the motion speed of pump head by using the inductive sensor and the metallic element. The at least one processor may be configured to monitor that the pump head is driven at a required speed by using the inductive sensor and the metallic element. The at least one processor may be configured to control the motor depending on a data relating to the speed of the pump head.

The at least one processor may be configured to detect at least of the following conditions:

- the angular position of the pump head relative to a flexible tube (for example the roller position relative to a flexible tube of a peristatic pump),
- a defective drive of the pump head,
- the angular speed of the pump head,
- a slippage of the pump head in relation to the drive mechanism, or
- the position of the metallic element relative to the pump head.

The at least one processor may be configured to control the pump head position (for example the angular position of the pump head relative to a flexible tube). The at least one processor can be configured to monitor the position of the pump head (e.g. the angular position of the pump head relative to a flexible tube) so as to move the pump head to a determined position (e.g. the determined angular position of the pump head relative to a flexible tube). These features can be useful for improving pumping accuracy.

The pump head may be driven by friction with the drive mechanism. The at least one processor may be configured to determine a slippage of the pump head relative to the drive mechanism. The at least one processor may be configured to control the motor depending on the slippage. The at least one processor may be configured to control the motor so as to avoid any slippage of the pump head relative to the drive mechanism.

The pump head may comprise at least one roller configured to compress the tube.

The metallic element may comprise at least one of a metallic paint (conductive), label, sticker, PCB (printed circuit board), any metallic highly conductive element, aluminum, and copper. The metallic element may have a strip shape, a square shape, a portion of an angle or some other curve shape. The inductive sensor may comprise an absolute encoder or an incremental encoder.

A second aspect of the disclosure provides a dialysis system comprising a medical pumping system as disclosed above.

A third aspect of the disclosure provides a medical system which may include or comprise:

- A reusable machine having a motor with a drive mechanism and controlled by a processing device, and A disposable cartridge having a pump head configured to be removably coupled to the drive mechanism of the machine and to be operatively coupled to a fluidic pathway so as to move a fluid through the fluidic pathway, The reusable machine may comprise an inductive sensor connected to the processing device, and the pump head may comprise a metallic element intended to cooperate with the inductive sensor of the machine. The processing device may be configured to detect a defective drive of the pump head based on the data received from the inductive sensor.

A fourth aspect of the disclosure provides a medical pumping system which may comprise:

A machine which may comprise a motor and a drive mechanism operatively coupled to the motor, and A pumping unit which may comprise at least one of a frame, a tube and a pump head.

The pump head may be configured to be rotatably driven by the drive mechanism while the frame may remain stationary relative to the machine in use. The pumping unit may be further configured to be removably coupled to the machine.

The machine may further comprise an inductive sensor and at least one processor connected to the motor and the inductive sensor (5). The pump head may further comprise a metallic element (for example only one element comprising metal) intended to cooperate with the inductive sensor of the machine.

A fifth aspect of the disclosure provides a medical pumping system for moving a fluid through a tube, the system may include or comprise:

A machine having a motor and a drive mechanism, and

A pump head configured to be removably coupled to the drive mechanism of the machine and may be configured to be operatively coupled to the tube.

The machine may comprise an inductive sensor and at least one processor (or processing device) connected to the motor and the inductive sensor. The pump head may comprise a metallic element (for example only one element comprising metal) intended to cooperate with the inductive sensor of the machine.

The pump head may be configured to rotate relative to the tube. The at least one processor may be configured to detect the angular position of the pump head relative to the tube.

A sixth aspect of the disclosure provides a medical pumping which may comprise at least one of:

A reusable part which may comprise a drive mechanism, and

A disposable part which may comprise a tube and a pump head.

The pump head may be arranged in such a way to be operatively coupled with the tube and may be configured to rotate relative to the tube in use. The disposable part may be configured to be removably coupled to the reusable part. The reusable part may be configured to be successively used with several disposable parts.

The reusable part may comprise an inductive sensor and a processor (or processing device) operatively coupled to at least one of the drive mechanisms and the inductive sensor. The pump head may comprise a metallic element (for example only one element comprising metal) intended to cooperate with the inductive sensor of the reusable part.

The reusable part may further comprise a pressure sensor configured to measure the pressure of the fluid downstream or upstream of the pump head. The pressure sensor can be operatively coupled to the processor to use the pressure data in addition to the inductive sensor data to detect at least of the aforementioned condition.

Main advantages of this solution:

No problem of clogging or aging,

Less sensitivity to EMI (ElectroMagnetic Interference),

Less mechanical constraints (distance between or position of the inductive sensor and the metallic element).

BRIEF DESCRIPTION OF DRAWINGS

The present invention will be better understood at the light of the following detailed description which contains non-limiting examples illustrated by the following figures.

LIST OF ELEMENTS

Figure 1:
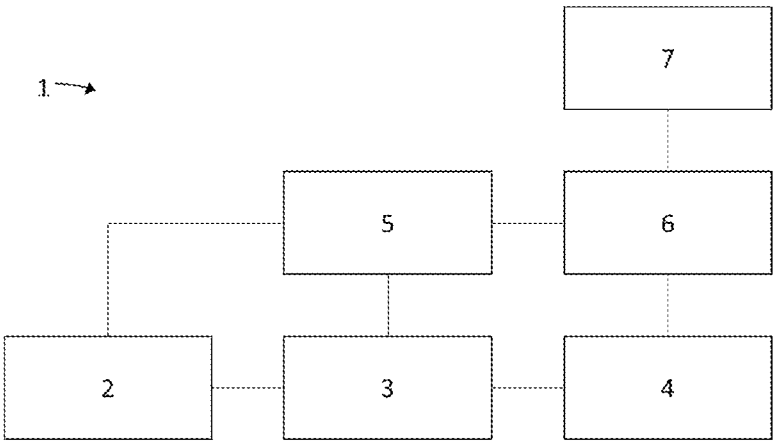
FIG. 1 illustrates an embodiment of the present disclosure.

| | |
|---|---|
| 1 | System |
| 2 | Processor |
| 3 | Motor |
| 4 | Drive mechanism |
| 5 | Inductive sensor |
| 6 | Pump head |
| 7 | Fluidic pathway |
| 10 | Dialysis system |
| 11 | Reusable apparatus |
| 12 | Disposable cartridge |
| 13 | Rotating part |
| 14 | Motor |
| 15 | Shaft |
| 16 | Inductive sensor |
| 17 | Metallic element |
| 18 | Processing device |
| 20 | Medical system |
| 21 | Reusable part |
| 22 | Disposable part |
| 24 | Electric motor |
| 25 | Drive mechanism |
| 26 | Inductive sensor |
| 28 | Processing device |
| 29 | Support |
| 30 | Roller |
| 31 | Holder |
| 32 | Target/Metallic element |
| 33 | Holder |
| 100 | Run motor |
| 101 | Data relating to pump head |
| 102 | Data processing |
| 103 | OK |
| 104 | NOK - 1 |
| 105 | Adapt actuation of the motor |
| 106 | NOK - 2 |
| 107 | Stop motor |
| 110 | Run motor |
| 111 | Data relating to motor |
| 112 | Data relating to pump head |
| 113 | Data processing |
| 114 | In range |
| 115 | Adapt actuation of the motor |
| 116 | Out of range |
| 117 | Stop motor |

DETAILED DESCRIPTION

In the following detailed description, reference is made to the accompanying drawings that form a part hereof, and in which are shown by way of illustration several embodiments of devices, systems, and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms “a”, “an”, and “the” encompass embodiments having plural referents, unless the content clearly dictates otherwise.

As used in this specification and the appended claims, any direction referred to herein, such as “top”, “bottom”, “left”, “right”, “upper”, “lower”, and other directions or orientations are described herein for clarity in reference to the figures and are not intended to be limiting of an actual device or system. Devices and systems described herein may be used in a number of directions and orientations.

As used herein, “have”, “having”, “include”, “including”, “comprise”, “comprising” or the like are used in their open ended sense, and generally mean “including, but not limited to.

As used herein, “at least one of A, B, and C”, “at least one of A, B or C”, “selected from the group consisting of A, B, C, and combinations thereof” or the like are used in their open ended sense including or comprising “only A, or only B, or only C, or any combination of A, B and C” unless the content clearly dictates otherwise.

As used in this specification and the appended claims, the term “or” is generally employed in its sense including or comprising “and/or” unless the content clearly dictates otherwise.

The present application claims the benefit of the priority of EP22198816.5 filed on Sep. 29, 2022 in the name of Nextkidney SA, the entire disclosure of which is incorporated herein by reference.

According to one embodiment (as shown by FIG. 1), the system (1) disclosed in this document includes or comprise at least one of A machine, A processor or processing device (2), A motor (3), A drive mechanism (4), An inductive sensor (5), A pump head (6), and A fluidic pathway (7).

The motor is coupled (e.g. mechanically) to the drive mechanism (4). At least one of the motor and the drive mechanism may be arranged into the machine (for example a reusable machine). The pump head (6) is configured to be removably coupled to the drive mechanism (4). When the pump head and the drive mechanism are operatively coupled, the drive mechanism may be configured to drive the pump head according to a parameter (which may be defined by the treatment or predetermined). In a possible embodiment, the pump head is frictionally driven by the drive mechanism.

In the case where the motor is a rotary motor, the drive mechanism may be fixed or operatively coupled to the shaft (rotor) of the rotary motor and the drive mechanism may drive a rotary motion of the pump head.

The pump head may comprise at least one roller (for example 2, 3 or more) configured to compress a (flexible) tube so as to move a fluid through the fluidic pathway (7) (which may comprise the tube) as a peristaltic pump does. The roller(s) may contact the drive mechanism to drive the pump head by friction.

The motor may comprise an electric motor (for example a brushless motor). The motor may be controlled by the processor so as to control the operation of the motor (for example the rotation speed of the motor).

The pump head (6) may comprise a metallic element intended to cooperate with the inductive sensor (5). The inductive sensor may be connected to the processor (and/or to another processor but to simplify the description only one processor is described here unless the content clearly indicates otherwise) so as to monitor the pump head. For example, the processor may monitor a status of the pump head such as the presence of the pump head, the position of the pump head, the angular position of the pump head relative to the tube or the frame, the position relative to inductive sensor, the rotary motion, the motion speed, the acceleration, the slippage (e.g. in relation to the drive mechanism) . . . .

To simplify the description, the present document may also use the term “processing device” or “control module” which may be arranged into the system and may comprise one or more processor(s).

In one embodiment, the processing device may control the motor speed and/or monitor a data relating to the pump head speed. The processing device may also monitor the motor speed. The processing device may be configured to process (for example compute, compare) the data relating to the speed motor and the data relating to the pump head speed and to determine an action based on these data processing.

In one embodiment, to monitor the pump head speed, the processing device may be configured to receive two angle measurements (e.g. angular position) separated by a predetermined time, then the pump head speed may be computed by the processing device based on these angle measurements.

In one embodiment, to monitor the pump head speed, the processing device may be configured to monitor the number of motor revolutions and the number of pump head revolutions (during a determined time period or during one pump head revolution), then the processing device may compare the data. The processing device may take into account a motor reduction ratio.

In one embodiment, the system may comprise two distinct processors, a first processor configured to control the motor and a second processor configured to receive the measurement of the inductive sensor (pump head speed). The first processor may also receive the measurement of the inductive sensor. In one embodiment, both processors receive same data and each processor (first and second) processes itself the data and each is able to alert the patient or trigger an action (alarm, correction, . . . )

The motor may further comprise its own sensor configured to monitor the operation of the motor. This sensor may send data to the processing device to monitor the proper operation of the motor itself. And the processing device may be configured to compare the data of the motor sensor to those of the inductive sensor (5). The motor sensor may be arranged with or in the motor and may be connected to the processing device.

The processor may be configured to launch or run action(s) depending on one or more condition(s) (e.g. threshold, operating range, . . . ). For example, if a slippage (e.g. the difference between the pump head speed and the motor speed or the difference between the expected/required pump head speed and the measured pump head speed) of the pump head occurs within a first operating range (due to a slight change in roller geometry, surface condition of the rollers), the motor speed may be adapted to keep a required speed of the pump head (e.g. without informing the patient). For example, if the slippage reaches a first threshold, the processor may adapt the motor speed such that the pump head speed can reach the required speed. And if a slippage of the pump head occurs within a second operating range, the processor may generate an alert (via the GUI (Graphical User Interface) or alarm), send a notification to the patient and/or stop the treatment. For example, if the slippage reaches a second threshold (which is different from the first), the processor may stop the motor.

In the event that the motor speed differs from the pump head speed and/or in the event that the pump head speed differs from the required or expected speed, the processor may act on the system. For example, the processor may stop the motor or increase or decrease the motor actuation (e.g., speed of rotation, . . . ), adapt the motor speed (e.g. to reach the required speed of the pump head) or act on other element(s) of the system (other motor, pump, valve, . . . ). In case where the system is a hemodialysis treatment system comprising a blood pump, one or more dialysate pump(s), one or more valve(s), if the pump head of the blood pump fails then all pumps may be stopped, and the valve may be closed and if one dialysate pump fails only the dialysate pump(s) may be stopped.

Figure 2:
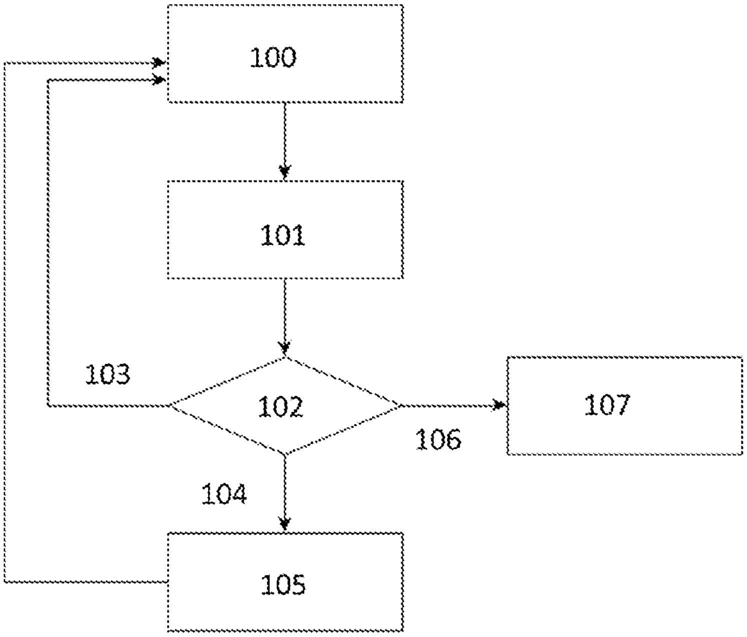
FIG. 2 illustrates a first flow chart.

For example, as shown in FIG. 2, the processing device may run the motor (100) and receive data relating to the pump head speed (101). The processing device may process the data (102) and determine if no problem has been detected (103), if a first failure (104) has been detected or if a second failure (106) has been detected. In case of first failure (104), the processing device may adapt the motor actuation (105) and in case of second failure (106), the processing device may stop the motor (107).

Figure 3:
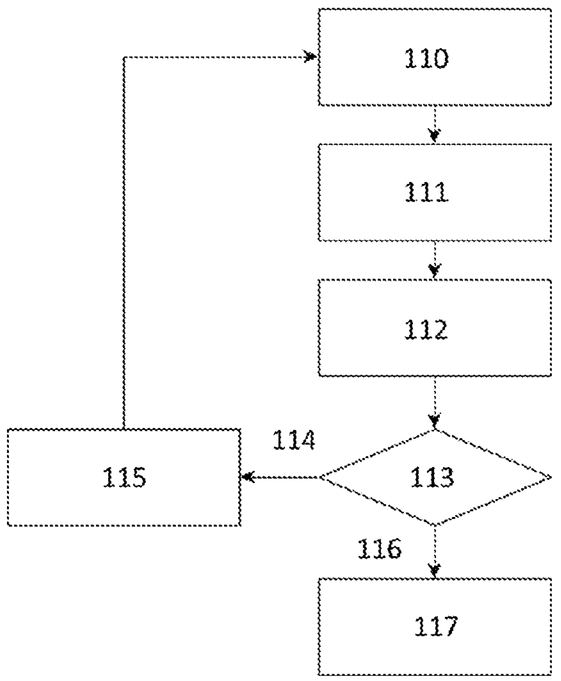
FIG. 3 illustrates a second flow chart.

For example, as shown in FIG. 3, the processing device may run the motor (110) and receive or retrieve data relating to the motor (111) (Sm) and data relating to the pump head speed (112) (Sph). The processing device may process the data (113) and determine whether it's within range (114) or out of range (116). If it's within range (114) then the processing device may adapt the motor speed (115) (if necessary) but if it's out of range (116) then the processing device may stop the motor (117).

In one embodiment, the system may have a reusable machine (or reusable part) and a disposable device (for example a cartridge) (or disposable part). The disposable device comprises the elements which have to be discarded after a predetermined number of uses, for example, after a single treatment. The working life of the disposable device may directly depend on the number of treatment. These elements may be the elements which have been wetted by the medical fluid (such as dialysate) or by the patient fluid (such as blood).

The disposable device may comprise at least one of a tube, a connector, a port, a shell, a frame, or a valve.

Preferentially, the reusable machine comprises the expensive elements for example the sensor, the electronic part, the screen, the actuator of the valve or of the pump, the processor or the memory. The reusable machine is successively used with several disposable device. The reusable machine may comprise components which may be replaced when the components are too worn, become broken or after a predetermined period of time, but much longer than a single treatment. The change of the reusable machine may depend on the component wear.

Example Applied to a Dialysis System

Figure 4:
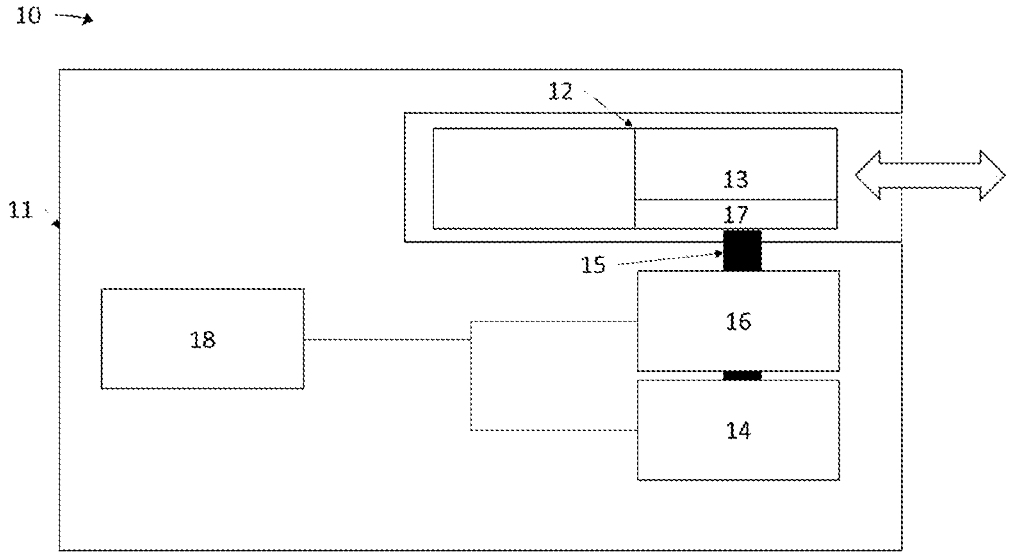
FIG. 4 illustrates an embodiment of the present disclosure.

According to an embodiment shown in FIG. 4, the dialysis system (10) comprises a reusable apparatus or machine (11) and at least one disposable cartridge (12). Preferentially, the reusable apparatus (11) comprises expensive elements (such as actuator, motor, sensor) while the disposable cartridge (12) includes or comprises the fluidic pathway such as tube and/or connectors. The dialysis system may be configured to removably receive the disposable cartridge (12).

The pumping device of the system may be a peristaltic pump comprising a fixed part arranged in the reusable apparatus (11) and a rotating part (13) arranged in the disposable cartridge (12). The fixed part may include or comprise a motor (14) (e.g. an electric brushless motor) having a shaft (15) (for example a floating shaft) configured to drive the rotating part (13) including or comprising at least one roller (for example three) maintained by a support having a hole configured to allow passage of the shaft (15).

For further details with regard to the floating shaft, reference may be made to U.S. Pat. No. 11,092,148 B2 or to European patent application EP 22186084.4, the contents of which are incorporated by reference in the present account.

Since the objective for the system is to be as quiet as possible, direct mechanical coupling (e.g. gears) between the shaft and the rollers may not be as advantageous as frictional drive. Therefore, the roller(s) may be frictionally driven with the shaft (15) and the system may monitor that the pump head is driven at the required speed and avoid any potential slippage.

As explained above, several types of sensors have been investigated. The use of an inductive sensor is particularly advantageous.

In a preferred embodiment, the reusable apparatus further includes or comprises an inductive sensor (16) and the cartridge (12) includes or comprises a metallic element (17) fixed on the rotating pump head (13) and configured to cooperate with the inductive sensor (16).

The metallic element (17) may be a metallic paint (conductive), label/sticker or a PCB (printed circuit board) and may comprise any metallic highly conductive element such as aluminum or copper with a thickness comprised between 1 and 100 μm, or 15 and 50 μm (for example 35 μm). In one embodiment, the shape of the metallic element is a half-circle/ring of copper on a PCB. However, according to the type of encoding (absolute vs incremental), the metallic element may have different shapes such as stripes, squares, portion of an angle or some other curve.

The metallic element must be or may be rigidly fixed on a rotating piece of the rotating part, for example on the pump head (rollers support) (13).

In one embodiment, due to the pump head small dimensions, the inductive sensor and the metallic element may form an absolute encoder. For example, a first PCB having a half-circle/ring of copper (used as metallic element) is glued on the pump head. The absolute encoder may be implemented by using a second PCB on the fixed part on which an integrated circuit is mounted and connected to three coils. These coils may be composed of transmitting coil and the two others are sine and cosine reception coils. As the metallic half circle on the second part (the first PCB) is facing the second PCB, the absolute angular position is obtained by computing the arctangent of sine/cosine signals. The division of the two sine and cosine signals has the advantage that it cancels most of the signal noise and gain, which removes the necessity of a calibration, and decreases sensitivity to the distance and relative position to the pump head.

In another embodiment, an incremental inductive encoder may use two ranges of stripes on the rotating part and two coils or pair of coils (depending on the sensor used) on the fixed part. Each coil may have respectively generated an A and B signal as an incremental encoder would.

The inductive sensor may be arranged to face the metallic element when the disposable cartridge is fully inserted into the reusable apparatus.

The absolute inductive encoder may be connected to a processing device (18). The processing device may comprise a first processor (called Main or Control) configured to control the pump and a second processor (called Protective) configured to monitor the pump head rotation. The absolute angular position may be retrieved by the processing device (18) periodically and may be used, in complement with the fixed pump motor encoder, to control the pump and monitor the possible slippage between the pump motor shaft and the rollers (pump head).

Another Example

Figure 5:
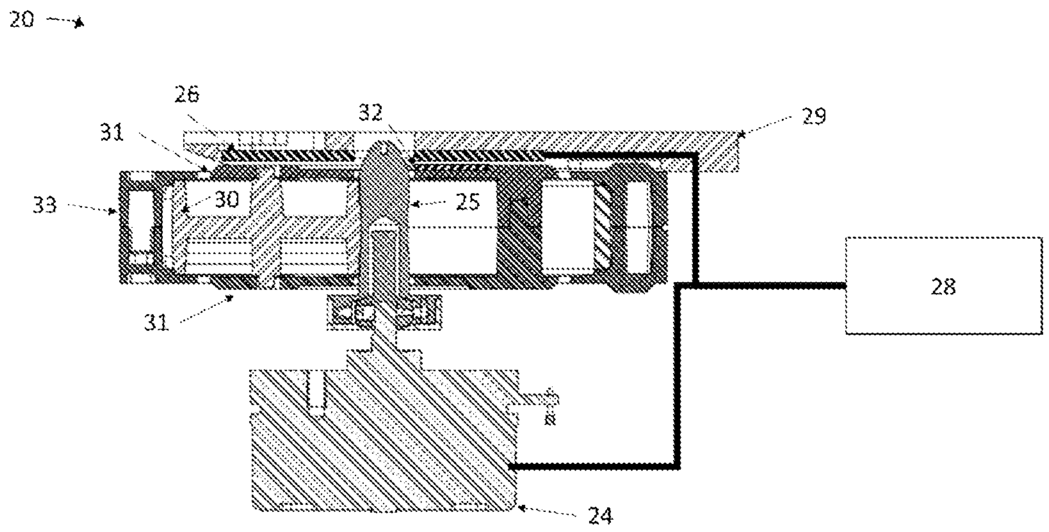
FIG. 5 illustrates an embodiment of the present disclose.
Figure 6:
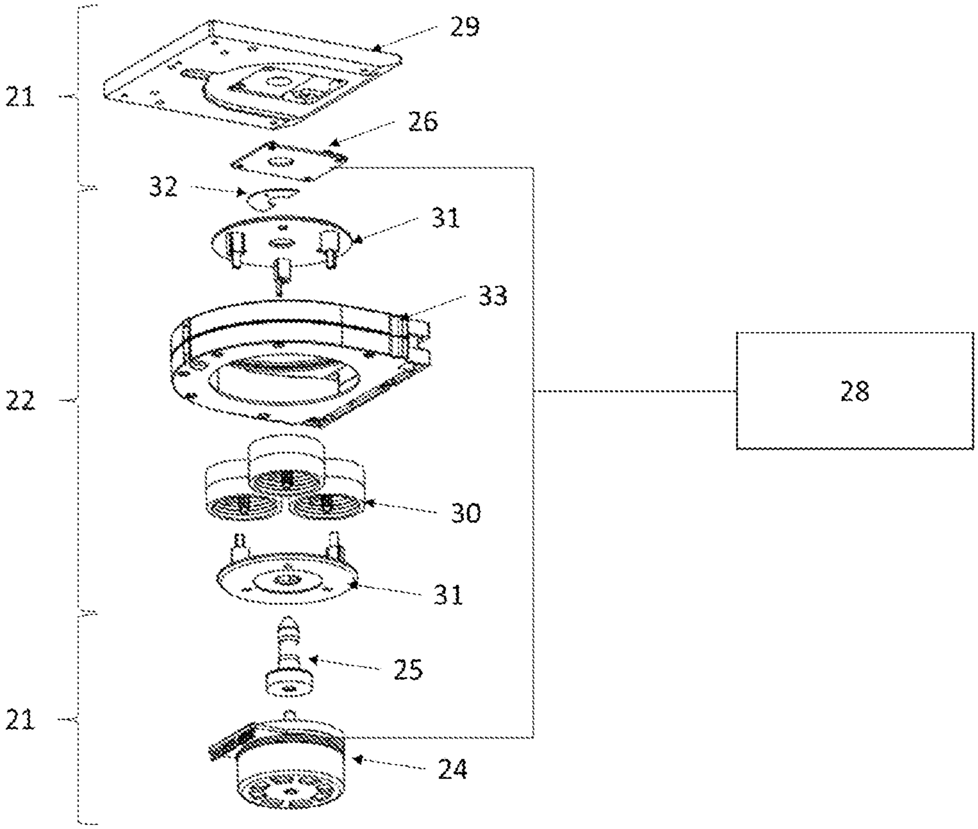
FIG. 6 illustrates an embodiment of the present disclosure.

As shown by FIGS. 5 and 6, the medical system (20) may comprise a reusable part (21) and a disposable part (22). The reusable part (21) may comprise an electric motor (24) having a drive mechanism (25), an inductive sensor (26) which may be secured on a support (29) of the reusable part (21). The Motor (24) and the inductive sensor may be electronically coupled to a processing device (28) which may comprise at least one processor.

The disposable portion (22) may be configured to be removably inserted into the reusable portion (21). The disposable portion (22) may comprise a rotatable portion having a roller assembly with one or more rollers (30) and a holder (31). The disposable portion may further comprise a target (32), having a metallic element, intended to cooperate with the inductive sensor (26) to provide information from the rotating portion to the processing device (28). The disposable portion (22) may further comprise a holder (33) of the rotatable portion (e.g., wherein the rotatable portion may have a rotational movement relative to the holder (33) or the reusable portion) which may comprise a flexible tube for being compressed by the at least one roller (30). The drive mechanism (25) may be configured to drive the roller by friction (through contact between the roller and the drive mechanism (for example the shaft and/or the rotor of the motor)).

The invention claimed is:

1. A medical pumping system for moving a fluid through a flexible tube, the system comprising:

a. a machine comprising a motor and a drive mechanism, and b. a pump head configured to be removably coupled to the drive mechanism of the machine, wherein the machine further comprises an inductive sensor and at least one processor, comprising processing circuitry, connected to the motor and the inductive sensor, wherein the pump head further comprises a metallic element intended to cooperate with the inductive sensor of the machine, wherein the pump head is configured to be driven by friction with the drive mechanism;

wherein the at least one processor is configured to determine a slippage of the pump head relative to the drive mechanism.

2. The system according to claim 1, wherein the motor is configured to drive a rotary motion of the pump head via the drive mechanism when the drive mechanism and the pump head is operatively coupled.

3. The system according to claim 1, wherein the at least one processor is configured to monitor a data relating to the motion speed of pump head by using the inductive sensor and the metallic element.

4. The system according to claim 1, wherein the at least one processor is configured to monitor that the pump head is driven at a required speed by using the inductive sensor and the metallic element.

5. The system according to claim 1, wherein the at least one processor is configured to control the motor depending on a data relating to the pump head speed.

6. The system according to claim 1, wherein the at least one processor is configured to control the motor depending on the slippage.

7. The system according to claim 1, wherein the at least one processor is configured to control the motor so as to avoid any slippage of the pump head relative to the drive mechanism.

8. The system according to claim 1, wherein the pump head comprises at least one roller configured to compress the flexible tube.

9. The system according to claim 1, wherein the metallic element comprises at least one of a metallic paint, label, sticker, printed circuit board, any metallic highly conductive element, aluminum, and copper.

10. The system according to claim 1, wherein the metallic element has a strip shape, a square shape, a portion of an angle or some other curve shape.

11. The system according to claim 1, wherein the inductive sensor comprises an absolute encoder or an incremental encoder.

12. The system according to claim 1, wherein the at least one processor is configured to determine an angular position of the pump head relative to the flexible tube and to control the motor so as to move the pump head to a specific angular position relative to the flexible tube.

13. A dialysis system comprising a medical pumping system according to claim 1.

14. A medical system comprising:

a. a reusable machine having a motor with a drive mechanism and controlled by a processing device comprising processing circuitry, and b. a disposable cartridge having a pump head configured to be removably coupled to the drive mechanism of the machine and to be operatively coupled to a fluidic pathway so as to move a fluid through the fluidic pathway, wherein the reusable machine further comprises an inductive sensor connected to the processing device, wherein the pump head further comprises a metallic element intended to cooperate with the inductive sensor of the machine, wherein the pump head is configured to be driven by friction with the drive mechanism;

wherein the processing device is configured to determine a slippage of the pump head relative to the drive mechanism.

15. The system according to claim 14, wherein the processing device is configured to control the motor depending on the slippage.

* * * * *